United States Patent
Richter et al.

[11] Patent Number: 5,843,311
[45] Date of Patent: Dec. 1, 1998

[54] ACCELERATED SOLVENT EXTRACTION METHOD

[75] Inventors: Bruce E. Richter, Sandy, Utah; Christopher A. Pohl, Union City, Calif.; Nathan L. Porter, Kaysville, Utah; Brian A. Jones, West Jordan, Utah; John L. Ezzell, Layton, Utah; Nebojsha Avdalovic, San Jose, Calif.

[73] Assignee: Dionex Corporation, Sunnyvale, Calif.

[21] Appl. No.: 259,667

[22] Filed: Jun. 14, 1994

[51] Int. Cl.⁶ .............................. B01D 11/00; B01D 11/02
[52] U.S. Cl. ......................... 210/634; 210/638; 210/639; 436/178
[58] Field of Search ..................................... 210/634, 656, 210/659, 198.2, 181, 638, 630; 436/178

[56] References Cited

U.S. PATENT DOCUMENTS

| | | |
|---|---|---|
| 1,856,567 | 5/1932 | Kleinert et al. . |
| 2,037,001 | 4/1936 | Aronovsky . |
| 2,733,135 | 1/1956 | Huckaby ................................. 436/178 |
| 3,209,676 | 10/1965 | Zimmermann et al. . |
| 3,327,613 | 6/1967 | Davis . |
| 4,438,816 | 3/1984 | Urban et al. ............................. 166/303 |
| 4,554,132 | 11/1985 | Collins . |
| 4,753,889 | 6/1988 | Collins ..................................... 436/178 |
| 4,770,780 | 9/1988 | Moses ..................................... 210/634 |
| 5,053,118 | 10/1991 | Houser ..................................... 208/45 |
| 5,087,360 | 2/1992 | Wright et al. ........................ 210/181 X |
| 5,133,859 | 7/1992 | Frank et al. ............................. 436/178 |
| 5,147,551 | 9/1992 | Averette . |
| 5,169,968 | 12/1992 | Rice ........................................ 554/193 |
| 5,170,727 | 12/1992 | Nielsen ................................... 110/346 |
| 5,255,205 | 10/1993 | Wurm et al. ............................. 364/510 |

FOREIGN PATENT DOCUMENTS

| | | |
|---|---|---|
| 0485668A1 | 11/1990 | European Pat. Off. . |
| 0 446 975 | 2/1991 | European Pat. Off. . |
| 41 29 195 | 3/1993 | Germany . |

OTHER PUBLICATIONS

Schnitzer, M. et al., "Supercritical Gas Extraction of a Soil with Solvents of Increasing Polarities₁", Soil Sci. Soc. Am J., vol. 51: 639–646 (1987).

Schnitzer, et al., "Supercritical Gas Extraction of Alkanes and Alkanoic Acids", Soil Sci. Soc. Am., vol. 30: 913–919 (1986).

Schnitzer, et al., "Organic Matter Extraction form Soils with Water at High Pressure and Temperatures", Soil Sci. Soc. Am J., vol. 55: 102–108 (1991).

Nielson, R. et al., "Extraction and Quantitation of Polyolefin Additives", Journal of Liquid Chromatography, vol. 41(3): 503–519 (1991).

Freitag, W. et al., "Fast Separation of Stabilizers from Plyolefins by Microwave Heating", Die Angewandte Makromolekulare Chemie, 175: 181–185 (1990).

Fernando, L. et al., "Closed–Vessel Microwave dissolution and Comprehensive Analysis of Steel by Direct Current Plasma Atomic Emission Spectrometry", Anal. Chem., vol. 58:511–512 (1986).

Fischer, L. et al., "Microwave Dissolution of Geologic Material: Application to Isotope Dilution Analysis", Anal. Chem., vol. 58: 261–263 (1986).

Kingston, H.M. et al., "Microwave Energy for Acid Decomposition at Elevated Temperatures and Pressures using Biological and Botanical Samples", Anal. Chem., vol. 58: 2534–2541 (1986).

(List continued on next page.)

Primary Examiner—Joseph W. Drodge
Attorney, Agent, or Firm—David J. Brezner

[57] ABSTRACT

Methods for the solvent extraction of organic analytes from a sample are provided. An organic solvent system is used to extract analytes under elevated temperatures and pressures above 100 psi but below supercritical conditions in short times and with low amounts of solvent. The extracted organic analytes are then removed by flowing a purge fluid through the extraction cell, the cell being maintained at a constant volume throughout the extraction and purging, afterwards the analytes being analyzed.

35 Claims, 1 Drawing Sheet

OTHER PUBLICATIONS

Rezaaiyan R. et al., "A Comparison of Mineral Extraction Techniques of Citrus Juices as Analyzed by Inductively Coupled Plasma Atomic Emission Spectrometry", *Journal of Food Science,* vol. 55(5): 1359–1360 (1990).

Nieuwenhuize, J. et al., "Comparison of Microwave and Conventional Extraction Techniques for the Determination of Metals in Soil, Sediment and Sludge Samples by Atomic Spectrometry", *Analyst,* vol. 116: 347–351 (1991).

Campbell, M. et al., "High–pressure Microwave Digestion for the Determination of Arsenic, Antimony, Selenium and Mercury of Oily Wastes", *Analysts,* vol. 117: 121–124 (1992).

Ganzler, K. et al., "Effective sample preparation method for extracting biologically active compounds from different matrices by a microwave technique", *Journal of Chromatography,* vol. 520: 257–262 (1990).

Ganzler, K. et al., "A New Method for the Extraction and High–performance Liquid Chromatographic Determination of Vicine and Convicine in Fababeans", *Chromatography,* pp. 435–443 (1984).

Mahan, K. et al., "Microwave Digestion Techniques in the Sequential Extraction of Calcium, Iron, Chromium, Manganese, Lead, and Zinc in Segments", *Anal. Chem.,* vol. 59: 938–945 (1987).

Ganzler, K. et al., "Microwave Extraction A Novel Sample Preparation Method for Chromatography" *Journal of Chromatography,* vol. 371: 299–306 (1986).

Hocquellet, P. et al., "Evaluation of Microwave Digestion and Solvent Extraction for the Determination of Trace Amounts of Selenium in Fees and Plant Animal Tissues by Electrothermal Atomic Absorption Spectrometry" *Analyst,* vol. 116: 505–509 (1991).

Capriel, P., et al., "Supercritical Methanol: An Efficacious Technique for the Extraction of Bound Pesticide Residues from Soil and Plant Samples", *J. Agric. Food Chem.,* vol. 34: 70–73 (1986).

Lautenschlaeger, W., "Microwave Digestion in a Closed–Vessel, High–Pressure System", *Spectroscopy International,* vol. 2(2): 18–22 (1990).

T.A. Berger, Packed Column SFC, RSC Chromatography Monographs, The Royal Society of Chemistry, p. 5, undated.

EPA Method 3540C, Soxhlet Extraction, Jan. 1995.

EPA Method 3541, Automated Soxhlet Extraction, Sep. 1994.

EPA Method 3550, Ultrasonic Extraction, Jan. 1995.

Majors, R., The Changing Role of Extraction in Preparation of Solid Samples; LC–GC vol. 14, No. 2, Feb. 1996.

Mangani, F. et al., Extraction of Low Molecular Weight Polynuclear Aromatic Hydrocarbons from Ashes of Coal–Operated Power Plants; Anal. Chem. 1987, 59, 2066–2069.

5,843,311

ACCELERATED SOLVENT EXTRACTION METHOD

FIELD OF THE INVENTION

Methods are provided for the solvent extraction of organic analytes from a sample in an organic solvent system under elevated temperatures and pressures below supercritical conditions.

BACKGROUND OF THE INVENTION

A number of systems have been used for the extraction and/or removal of compounds and analytes from solid or semi-solid samples for quantification and identification.

Soxhlet extraction has been in use for over 100 years. In this technique, the extraction of analytes takes place at or close to room temperature, over a period of several hours to several days, and generally uses a large volume of solvent to sample ratio. Fast Soxhlet extractions are also done at the boiling point of the solvent; this system is sold under the tradename "SOXTEC" and is manufactured by Perstorp, Inc. A similar system is marketed under the tradename "SOXTHERM" and is made by ABC Laboratories. For example, an automated Soxhlet extraction technique is used in the Environmental Protection Agency (EPA) method 3541 for the extraction of organic analytes from soil, sediment, sludges and waste solids.

Microwave extraction has also been used, which provides shorter extraction times due to faster heat up times. U.S. Pat. No. 4,554,132 describes an apparatus for the use of microwave for drying the sample combined with solvent extraction at atmospheric pressure in unsealed vessels. Other techniques have been described for the preparation of samples for chromatography, ICP (Inductively Coupled Plasma Emission Spectroscopy) and amino acid analysis (U.S. Pat. No. 4,554,132; P. Hocquellet and M.-P. Candillier, *Analyst, 116*:505–509 (1991); K. Ganzler, A. Salgó and K. Valkó, *J. Chromatography,* 371:299–306 (1986); K. Ganzler, J. Báti and K. Valkó, *Akadémiai Kiadó, Chromatography '84, Budapest, Hungary*, H. Kalász and L. S. Ettre, eds., pp.435–442 (1984); K. Ganzler, I. Szinai and A. Salgó, *J. Chromatogr.,* 520:257–262 (1990); K. I. Mahan, T. A. Foderaro, T. L. Garza, R. M. Martinez, G. A. Maroney, M. R. Trivisonno and E. M. Willging, *Anal. Chem.,* 59:938–945 (1987)) using microwave extraction in unsealed vessels.

Sealed vessels have also been described (refs 7–13) in conjunction with microwave extractions (L. A. Fernando, W. D. Heavner and C. C. Gabrielli, *Anal. Chem.,* 58:511–512 (1986); L. B. Fischer, *Anal. Chem.,* 58:261–263 (1986); H. M. Kingston and L. B. Jassie, *Anal. Chem.,* 58:2534–2541 (1986); R. Rezaaiyan and S. Nikdel, *J. of Food Science,* 55:1359–1360 (1990);; J. Nieuwenhuize, C. H. Poley-Vos, A. H. van den Akker and W. van Delft, *Analyst,* 116:347–351 (1991); M. B. Campbell and G. A. Kanert, *Analyst,* 117:121–124 (1992)). These sealed vessels allow the use of higher pressures and temperatures; for example, reported pressures vary from 40 psi (L. A. Fernando, W. D. Heavner and C. C. Gabrielli, *Anal. Chem.,* 58:511–512 (1986); L. B. Fischer, *Anal. Chem.,* 58:261–263 (1986)) to 3000 psi (W. Lautenschlaeger, *Spectroscopy International,* 2:18–22 (1990)). These systems are utilized to dissolve or digest the sample completely, and typically in large volumes of solvent.

For example, microwave extraction has been used to extract additives and stabilizers from polyolefins (W. Freitag and O. John, *Die Angewandte Makromoiekulare Chemie,* 175:181–85 (1990); R. C. Nielson, *J. Liq. Chromatogr.,* 14:503–519 (1991)). In these examples, the polyolefins are ground and added to an excess of solvent, heated in a microwave, and the solvent containing the analyte is analyzed. In some cases the solvent was evaporated prior to analysis.

European Patent Application 0 485 668 A1 describes a flow through system utilizing a solvent system to extract volatile oils from biological materials. In this system, the biological material is placed in an organic solvent and exposed to microwave energy. The local heating of the biological material causes an increased pressure in the cells until they burst and release their contents into the cooler solvent.

U.S. Pat. No. 5,147,551 describes an apparatus used in extraction. A sample is placed in a sealed vessel with a frit. Solvent, which may be heated or unheated, is introduced into the vessel, which may also be heated. After a soak period, an inert gas is swept up through the frit and through the sample to remove the volatile analytes, and then the gas is analyzed, for example on a gas chromatograph.

Extraction has also been done using solvents under supercritical conditions (P. Capriel, A. Haisch and S. U. Kahn, *J. Agric. Food Chem.,* 34:70–73 (1986); M. Schnitzer, C. A. Hindle and M. Meglic, *Soil Sci. Soc. Am. J,* 50:913–919 (1986); M. Schnitzer and C. M. Preston, *Soil Sci. Soc. Am. J.,* 51:639–646 (1987)).

Finally, soil has been extracted using water as the solvent at elevated temperatures and pressures below supercritical conditions (M. Schnitzer, H.-R. Schelten, P. Schuppli and D. A. Angers, *Soil Sci. Soc. Am. J.,* 55:102–108 (1991)).

However, the drawbacks associated with all of these techniques include lengthy extraction times and a large ratio of solvent to sample, resulting in solvent disposal considerations. Thus a fast extraction method which utilizes a minimum of solvent would be desirable.

SUMMARY OF THE INVENTION

It is an object of the present invention to provide methods for the extraction of organic analytes from a sample with short processing times and low volumes of solvent.

Accordingly, in one aspect of the present invention a method is provided for solvent extraction of organic analytes from a sample. The method comprises maintaining a particulate sample containing an analyte in contact with a non-aqueous organic solvent system in an extraction cell. The cell is maintained under elevated temperatures and pressures below supercritical conditions for a sufficient time to extract at least a portion of the analyte. The organic solvent system is in liquid form under the operating conditions. The dissolved analyte is then removed by flowing a purge fluid through the extraction cell.

In one aspect, the volumetric ratio of said organic solvent system to said extraction cell is no greater than 5:1. In another aspect, the volumetric ratio of said organic solvent system to said sample is no greater than 5:1.

In another aspect of the invention, a flow-through method is provided for solvent extraction of organic analytes from a sample. The method comprises flowing a non-aqueous organic solvent system through a sample containing an analyte in an extraction cell under elevated temperatures and pressures below supercritical conditions. The solvent system flows through the sample at a rate sufficient to allow extraction, and the total volume of the organic solvent used during extraction does not exceed five times the volume of the extraction cell.

In the methods of the present invention, the extraction preferably is performed in the absence of microwave energy.

DETAILED DESCRIPTION OF THE INVENTION

Figure 1:
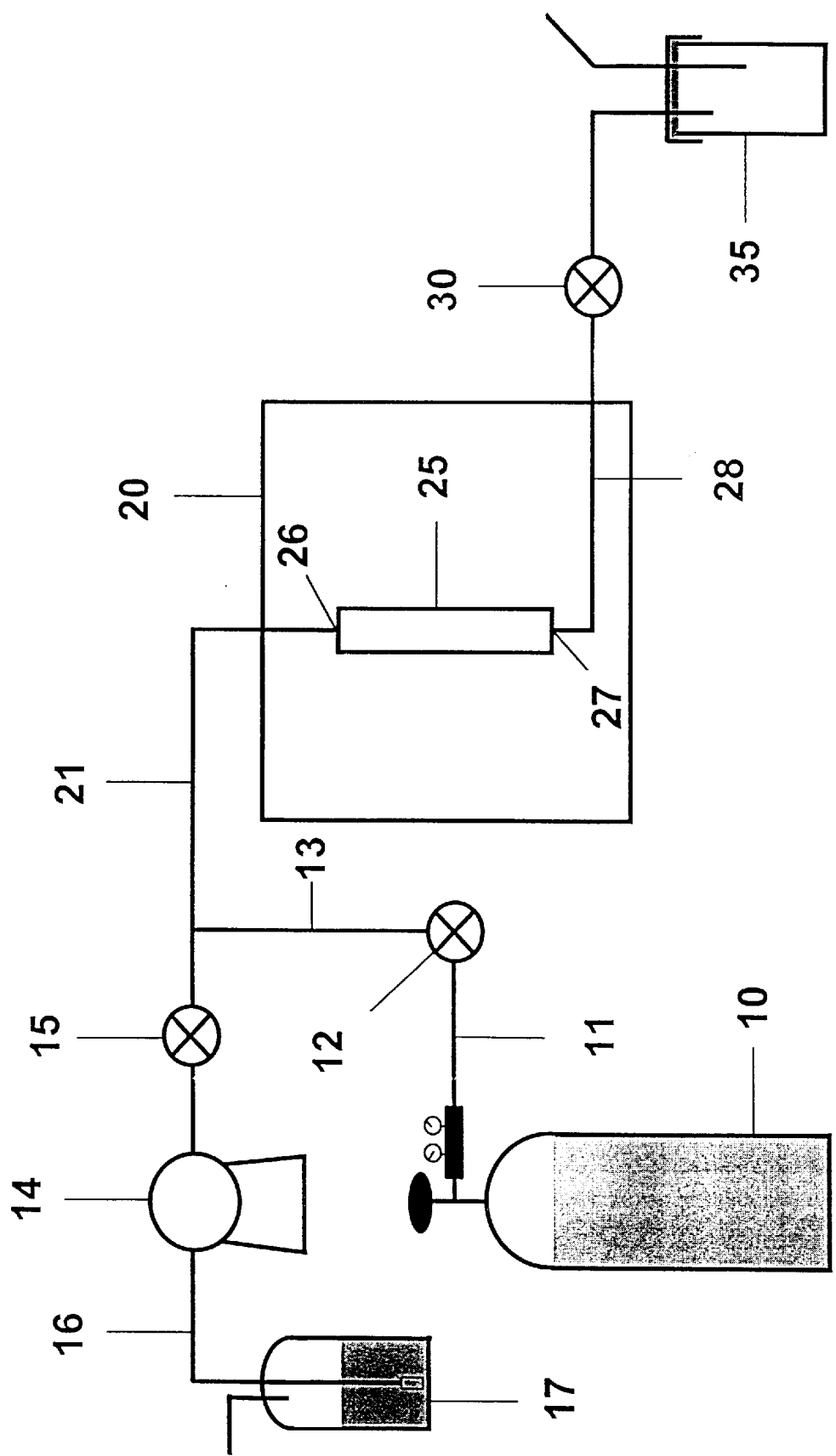
FIG. 1 depicts a representative apparatus for the solvent extraction methods of the present invention.

The present invention provides methods for the extraction of organic analytes from a sample using an organic solvent system.

It is useful in the extraction of a variety of organic analytes from different samples. The sample is the material containing the analytes to be extracted. An analyte may be a contaminant, impurity or additive to a sample, or it may be the main or major ingredient of a sample. For example, contaminants from soils, waste solids, sludges, sediments, food products, and animal and plant tissues such as leaves, cellulosic products, roots, and bark may all be analyzed using the present invention. Additives from samples such as polymers, resins, food products, pharmaceutical preparations or compositions and wood products may be analyzed. Impurities in samples such as food products, pharmaceutical preparations and polymers may be examined. Alternatively, the main or major ingredients of samples such as pharmaceutical preparations, food products, polymers or plant tissues may be evaluated.

Generally, the analytes are organic; that is, they are typically more soluble in organic solvents than in water or other aqueous solvents. Suitably, the analytes include, but are not limited to, pesticides, herbicides, PCBs, PAHs, gasoline components, triglycerides, phenols, aldehydes, alcohols, lipids, waxes, polymer additives, food additives, hormones, vitamins, hydrocarbons, chlorinated hydrocarbons, nitrosamines, phthalates, halogenated esters, heterocyclic compounds, acids, bases, pharmaceutical compounds, drugs, or mixtures thereof.

In one instance, the sample is either a solid or includes solids as a major component. Preferably, the samples are solid particles in the absence of substantial amounts of background liquid, typically water. Preferably, the water content in the sample should less than about 5–50, and preferably less than 20 wt %. High concentrations of water in the sample or sample should be avoided, due to the resulting complications using the organic solvents (i.e. poor sample penetration and channeling of the solvent through the sample). However, most samples contain some water and may be analyzed without further treatment. For example, samples such as sediments, sludges, food products and plant and animal tissues, which may be up to 80 wt % water, may be used without further treatment, or they may be dried as shown below. In a preferred embodiment, the sample is a solid particulate. Solid samples may be ground or pulverized, using sonication or other methods known in the art, to allow better extraction of the analyte. If the sample is ground, excessive heating should be avoided, to avoid loss of volatile analytes or altering the chemical nature of the analytes.

In some cases, the sample is normally a liquid or a gas. In this embodiment, the sample is stabilized on a solid substrate including, but not limited to, polyurethane foams, glass fiber support beds and filters, cellulose filters, polymer filters, polymeric resins, sodium sulfate, magnesium chloride, sand and diatomaceous earth.

If the samples contain an excess of water, the sample may be treated to remove most or all of the water while retaining the analytes. This may be accomplished in a variety of ways well known in the art, including heat treatment, evaporation, or treatment with desiccants such as acetone or ethanol. If heat is used, care should be taken to avoid destroying or eliminating volatile analytes.

The organic solvent system of the present invention is substantially non-aqueous, that is, the system consists essentially of organic solvent. By "substantially non-aqueous" or grammatical equivalents herein is meant that the solvent or mixture of solvents do not contain an appreciable amount of an aqueous solvent such as water. For example, the solvent system will comprise less than about 10%, and preferably less than about 5%, and most preferably about 0% (not more than trace amounts) of water.

A wide variety of organic solvents may be utilized in the organic solvent system, depending on the analyte to be extracted, as discussed below. Suitable general solvent classes include, but are not limited to, $C_1$–$C_6$ alcohols, halogenated hydrocarbons, saturated hydrocarbons, aromatic hydrocarbons, ketones, ethers, alcohol ethers, nitrogen-containing heterocyclics, oxygen-containing heterocyclics, esters, amides, sulfoxides, carbonates, aldehydes, carboxylic acids, nitrites, nitrated hydrocarbons and acetamides.

The organic solvent system of the present invention suitably has an average viscosity that ranges from about 0.20 to about 4.20 cps at 25° C. A preferred embodiment utilizes solvents with a viscosity range of about 0.2 to about 1.0 cps at 25° C., with the most preferred range being between about 0.20 to about 0.65 cps at 25° C.

Additionally, the solvents are chosen such that the ratio of the average viscosity of the solvent system at room temperature to its average viscosity at the operating temperature ranges from about 2 to about 15. The largest changes in average viscosity are seen with the solvents with the highest viscosity. A preferred embodiment utilizes a ratio of about 2 to about 10, with the most preferred ratio ranging from about 2 to about 5. The lower viscosities associated with high operating temperatures (50° to 250° C.) are preferred due to better penetration of the sample by the solvent.

If the solvent system used for extraction consists of a single solvent, those skilled in the art can calculate the change in viscosity of the solvent at various temperatures using, for example, the equations and graph shown in Perry's Chemical Engineers' Handbook, 6th Edition, Ed. R. Perry, page 3-281. Thus, for example, the viscosities of several solvents at different temperatures was calculated for Table 1:

TABLE 1

| Solvent | Viscosity at 25° C. | Viscosity at 150° C. | Viscosity at 200° C. |
| --- | --- | --- | --- |
| Water | 1.00 | 0.22 | 0.15 |
| Acetone | 0.316 | 0.13 | 0.11 |
| Acetonitrile | 0.345 | 0.14 | 0.10 |
| Methylene Chloride | 0.420 | 0.15 | 0.12 |
| Toluene | 0.560 | 0.16 | 0.13 |
| Ethanol | 1.10 | 0.22 | 0.15 |
| Hexane | 0.294 | 0.11 | 0.09 |
| Methanol | 0.547 | 0.16 | 0.13 |
| Isopropyl Alcohol | 2.13 | 0.40 | 0.23 |
| Chlorobenzene | 0.75 | 0.19 | 0.14 |
| Chloroform | 0.542 | 0.16 | 0.13 |
| Cyclohexane | 1.00 | 0.22 | 0.15 |

TABLE 1-continued

| Solvent | Viscosity at 25° C. | Viscosity at 150° C. | Viscosity at 200° C. |
|---|---|---|---|
| Dichlorobenzene | 1.32 | 0.28 | 0.18 |
| 2-Methoxyethanol | 1.65 | 0.30 | 0.20 |
| N-Methyl-pyrrolidone | 1.67 | 0.31 | 0.21 |
| Trimethylpentane | 0.470 | 0.15 | 0.12 |
| 2-Butanol | 4.2 | 0.5 | 0.30 |

If the solvent system comprises two or more solvents, the average viscosity of the mixture at 25° C. is determined using techniques well known in the art, and then the change in viscosity as a function of temperature is calculated as above.

The organic solvent system can be a single solvent or a mixture of solvents. Generally, mixtures of solvents will contain at least two, and may contain as many as 5–10 solvents. The solvents include, but are not limited to, perchloroethylene, iso-octane (also called trimethylpentane), hexane, acetone, methylene chloride, toluene, methanol, chloroform, ethanol, tetrahydrofuran, acetonitrile, methyl ethyl ketone, pentane, N-methylpyrrolidone, cyclohexane, dimethyl formamide, xylene, ethyl acetate, chlorobenzene, methoxyethanol, morpholine, pyridine, piperidine, dimethylsulfoxide, ethoxyethanol, isopropanol, propylene carbonate, petroleum ether, diethyl ether, dioxane, and mixtures thereof.

In one embodiment, additives are added to the organic solvents, typically to increase the solvent strength of a solvent. The additives may be chosen such that ionization of the analytes are suppressed, which allows the analytes to become more soluble in the organic solvent. Preferred additives include, but are not limited to, trifluoroacetic acid, citric acid, acetic acid, trimethyl amine, and tetramethyl ammonium hydroxide.

The selection of the solvents to be used in the extraction of any particular analyte is done in several ways. For example, if the sample and/or the analyte has a standard extraction procedure known in the art, the same solvent system may be used in the present invention. For instance, the EPA has numerous accepted protocols for the analysis of certain analytes and/or samples such as soils and sludges, which outline suitable solvents to use for particular analytes.

In an alternative embodiment, the chemical characteristics of the analyte are exploited to determine a suitable solvent system. Thus, analytes which are known to be soluble in a particular solvent or mixture of solvents may be extracted using that solvent system. Typically, the solubility of the analyte in the solvent system should be at least about from 0.001 gm/cc to 0.5 gm/cc, although solubilities of more than about 1 gm/cc as well as lower solubilities may be acceptable.

Solvents may also be chosen on the basis of their Hildebrand solubility parameters. For example, generally the solvents utilized in the present invention have Hildebrand solubility parameters between the parameter of pentane, 7.05, and methanol, 14.0. Hildebrand solubility parameters are known in the art; for example, Giddings et al., Science 162:67–73 (1968) contains a partial list.

Alternatively, those skilled in the art will employ other characteristics of the analytes. For example, analytes with known polarity will be extracted using a solvent with a compatible polarity index. Thus, a preferred embodiment utilizes solvents which have a polarity index between the polarities of pentane (polarity index of 0.0) and of dimethylsulfoxide (polarity index of 7.2). The polarity indices of a variety of suitable solvents are found in "High Purity Solvent Guide", Burdick and Jackson Laboratories, Inc., distributed by American Scientific Products.

Alternatively, solvents may be chosen on the basis of their dielectric constant. Generally, the dielectric constant of the solvent system ranges between the dielectric constant of hexane (1.88) and of propylene carbonate (69.0). The dielectric constants of a variety of suitable solvents are found in "High Purity Solvent Guide", Burdick and Jackson Laboratories, Inc., distributed by American Scientific Products.

Additionally, the solvents may be chosen on the basis of their dipole moment. Generally, the dipole moment of the solvent system ranges between the dipole moment of trimethylpentane (iso-octane) at 0.0 Debye and of N-methylpyrrolidone at 4.09 Debye. The dipole moments of a variety of suitable solvents are found in "High Purity Solvent Guide", Burdick and Jackson Laboratories, Inc., distributed by American Scientific Products.

In an alternative embodiment, the solvents are chosen on the basis of their eluotropic value on alumina. In this embodiment, the eluotropic value on alumina of the solvent system ranges between the eluotropic value of pentane (0.0) and of methanol (0.95). The eluotropic value of a variety of suitable solvents is found in "High Purity Solvent Guide", Burdick and Jackson Laboratories, Inc., distributed by American Scientific Products.

If the sample to be extracted contains unknown analytes, the determination of a suitable solvent system may be done in a variety of ways. For example, a sample may be divided up and extracted using different solvents. Thus, a variety of solvents will be tested; for example, a non-polar solvent, a slightly polar solvent and a highly polar solvent may all be tried. A comparison of the extracted analytes using known detection systems allows a determination of the best solvent for a particular analyte. Similar ranges may be tried based on any number of solvent and analyte properties.

In an alternative embodiment, a sample may be repeatedly extracted using different solvents, and the extracted analytes compared as above. Generally this will be done using a series of solvents with a range of characteristics, for example non-polar, slightly polar, and highly polar solvents. Alternatively, solvents may be chosen based on different characteristics, such as polarity, dipole moment, viscosity, dielectric constant, etc. In this way a range of solvent characteristics may be tested to determine a suitable or optimum solvent for any particular analyte.

Once the solvent system is chosen, extraction proceeds for example, using the apparatus shown in FIG. 1. Briefly, a compressed gas container 10 is linked, via line 11, to valve 12 and line 13 to valve 15, which is also connected to pump 14. The pump 14 in connected to a solvent reservoir 17 via line 16. Valve 15 is connected via line 21 to an inlet port 26 of extraction cell 25, which has an outlet port 27 connected via line 28 to valve 30. Valve 30 empties into a vial 35. The extraction cell 25 is contained within an oven 20.

The method proceeds as follows. First, the extraction cell 25 is loaded with sample containing the analyte or analytes of interest. In a preferred embodiment, the sample substantially fills the cell, that is, the dead volume of the cell is kept to 10% or less, although in some cases, compression of the sample during extraction may occur, causing a dead volume to occur. However, the void volume of the sample may be higher than 10%. This filling of the extraction cell allows uniform flow through the sample with high yields of extraction. Thus, the size of the extraction cell preferably is chosen to allow the sample to fill the cell completely. Suitable extraction cells have volumes of 0.5 ml to 32 mls, with 5 ml, 10 ml and 15 ml extraction cells being preferred, although other sizes may be used as well. In addition, the extraction cells are constructed of materials which allow the use of high pressures and temperatures. Suitable extraction cells include cells used in supercritical fluid extraction, and generally have frits of some type to retain the sample in the cell, as will be appreciated by those skilled in the art.

In alternative embodiments, the volume of the sample is less than the volume of the extraction cell, and an inert filler is used to load the extraction cell to capacity. In some cases, inert fillers may be used if the sample is highly compressible, which can lead to clogging of the system. Suitable inert fillers include solid particulate substances which do not contain extractable materials, such as sand, diatomaceous earth or glass wool. Other inert fillers will be readily ascertainable by those skilled in the art.

Once the extraction cell is loaded with sample, it is attached via its inlet and outlet ports to the pump and the sample collection vial. In one embodiment, the extraction cell is placed within the preheated oven or heating block and allowed to equilibrate to the oven or block temperature with a preferred equilibration time of 5 to 15 minutes. Alternatively, the solvent may be preheated to the desired temperature prior to contact with the sample. Also, the solvent and the sample may both be preheated. Preheating of either sample or solvent is not necessary, as outlined below.

Once the cell containing the sample is loaded and optionally preheated, the extraction may proceed in two ways, either with a static extraction step or in a dynamic, flow through mode.

A static extraction step is preferred. In this method, the solvent is pumped into the extraction cell with static valve 30 open, flow is established through the cell and a small amount, usually about 1 ml, is collected at the outlet. Valve 30 is then closed, and the system is pressurized to the appropriate pressure. Suitable pressures will depend on the particular solvents and samples of the run; for example, samples with high levels of extractable materials generally require less pressure. Suitably, the pressure ranges from about 100 to about 2500 psi. Preferred pressures range from about 1000 to about 2000 psi, with the most preferred pressure being about 2000 psi.

Once valve 30 is closed, the extraction cell is placed in the oven and the sample is brought up to temperature. As for the pressure, the exact temperature to be used will depend on the solvents and the analytes. Generally, the temperature in °K is maintained at a level of about 0.8 to 2.0 times the average boiling point in °K of the organic solvent system under standard conditions. A preferred temperature in °K ranges from about 1.0 to about 2.0 times the average boiling point, with the most preferred range being between about 1.0 to about 1.6 times the average boiling point.

The average boiling point in either °K or °C. can be determined using techniques known in the art. If the organic solvent system comprises a single solvent, the boiling temperature is ascertainable by reference to standard chemical charts. If the organic solvent system comprises two or more solvents, the average boiling temperature under standard conditions (at atmospheric pressure) can be readily determined using techniques known in the art.

The temperatures and pressures used in the method of the present invention are below supercritical conditions. That is, the solvent systems are in liquid form prior to extraction, at standard temperatures and pressures such at 25° C. and atmospheric pressure. In addition, the solvents remain liquid during extraction, due to the pressures used during extraction. Thus, even if the temperature is above the boiling point of the solvent system used, the solvent system remains liquid during extraction.

The cell is kept under pressure and temperature for a period of time. When the extraction is run without a preheat step, the time of extraction includes the time it takes for the extraction cell and sample to reach the target temperature. Generally, it takes the cell about 5 minutes to reach the target temperature, although longer or shorter times may be necessary depending on the system used. After the cell has reached the target temperature, extraction proceeds for sufficient time to extract at least a portion of at least one of the analytes from the sample. Generally this time ranges from about 5 minutes to 30 minutes, with the preferred time being from about 5 minutes to about 15 minutes, and the most preferred time being from about 5 to about 10 minutes. Under certain circumstances, extraction times of up to an hour may be required.

The time sufficient to extract the analytes from the sample may be determined in several ways, and will depend in part on the purpose of the extraction. For example, if qualitative identification of analytes is of primary importance, then a less efficient extraction may be done. Alternatively, if the quantitation or yield of the analytes is important, a more complete extraction is desirable.

In a preferred embodiment, the extraction is run such that not more than about 20%, and preferably not more than 10%, more of the analyte or analytes will be subsequently extracted in a subsequent extraction using the same method or other extraction methods such as Soxhlet or microwave extraction. Thus, the time of extraction is chosen such that at least about 80–90% of the extractable analytes are extracted. Generally, as outlined above, this time ranges from 5 to 30 minutes for the average sample. One measure of sufficient extraction is that no more than about 10% more of the analytes would be extracted by maintaining the same extraction conditions for an additional hour. As will be appreciated by those skilled in the art, sample extraction may be discontinuous. In that event, the time is the total time of extraction.

In a preferred embodiment, when the sample is a solid matrix, it is not dissolved during extraction, but rather the analytes removed. Thus the conditions of the reaction are designed to avoid the complete solubilization of a solid matrix. However, as one skilled in the art will appreciate, solid matrices containing significant amounts of analytes may show a decrease in mass as a result of the extraction of the analytes.

Once the static time is complete, the static valve 30 is opened, a volume of flush fluid (approximately 1 to 5 ml) is pumped into the cell. The flush fluid is a liquid solvent which is introduced into the cell, prior to removing the solvent system containing the extracted analytes, to minimize analyte loss in the removal step. The flush fluid may be the same solvent system used in the extraction, or another liquid solvent. Then valve 15 is closed and valve 12 is opened to allow a purge fluid, i.e. a fluid which will displace the solvent system containing the extracted analytes from the sample, to drive the solvent containing the analytes out of the extraction cell into the collection vial 35. The collection vial may be under pressure, or may be at atmospheric pressure. The vial may be unsealed, or sealed and under an atmosphere of air or inert gas, such as the one used as the purge fluid. The purge fluid may be an inert gas, such as helium, nitrogen or carbon dioxide, or in some circumstances it may be another solvent. Alternatively, the purge fluid may be the same solvent system as used in the extraction. The lines may then be flushed with fresh solvent and the extraction cell is removed and cleaned for the next use.

The amount of solvent needed to extract the analytes using the methods of the present invention will vary. Generally, the amount of solvent used is kept to a minimum, and is usually the amount of solvent contained within the cell during extraction, i.e. the solvent in the void volume. Suitably, the ratio of the volume of organic solvent to the volume of the extraction cell ranges from 1:1 to 5:1, preferably in the ratios of 1.2:1, 1.5:1, 2:1, 3:1 and 4:1. In an alternative embodiment, when the sample fills the cell, the ratio of the volume of organic solvent to the volume of the sample ranges from 1:1 to 5:1, with 1.2:1, 1.5:1, 2:1, 3:1 and 4:1 also preferred. Similarly, the ratio of the volume of the organic solvent to the weight of the sample typically falls in the range of from about 1:1 in mls/gm to 5:1 mls/gm.

In an alternative embodiment, the extraction is performed in a dynamic, flow-through mode. In this embodiment, the loading of the extraction cell and pressurization of the cell proceeds as above. In this case, a preheating step prior to the introduction of the solvent is preferred. After preheating, solvent is flowed slowly through the cell and collected. Those skilled in the art will appreciate that the faster the flow rate, the less efficient the extraction, but that higher flow rates may be appropriate for larger extraction cells or samples with large quantities of extractable material. Thus generally the flow rates range from about 0.1 to about 5 ml/minute, with a preferred range from about 0.1 to about 0.5 ml/min, when the cell volume is 0.5 to 10 ml. In this embodiment, the total volume of the organic solvent needed for the extraction ranges from about twice the volume of the extraction cell to about five times the volume of the extraction cell.

In an alternative embodiment, both static and dynamic extraction may be done. For example, as shown in the Examples for fat extraction, the system may have a static step, followed by a flow through step. This may be repeated several times if desired.

Preferably, the extraction is run in the absence of microwave energy. In some embodiments, microwave energy may be used to dry a sample as outlined above, but not during the extraction process.

Once the analytes dissolved in the solvent are obtained, they are usually detected or analyzed. This may be done in a variety of ways, depending on whether identification or quantification of the analytes is desired, and on the composition of the analytes. The analytes may be retained in the solvent, or the solvent removed, for example by evaporation. Generally, the analytes are analyzed using techniques well known in the art, including, but not limited to, application of gas chromatography, mass spectrometry, ion chromatography, liquid chromatography or capillary electrophoresis. In addition, the solvent system containing the analytes may be concentrated prior to analysis, for example by inert gas blow-down or evaporation. If the concentration of analytes is high, the analytes may also be diluted prior to analysis by adding solvent, for example.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXAMPLES

Example 1

Solvent Extraction of Pesticides from a Spiked Standard Soil

The apparatus was set up as shown in FIG. 1, and is made of standard HPLC hardware. Conditions for example 1 and 2 are summarized in Table 2. For sample 1, a 10.4 ml capacity cell was loaded with 10 gm of a standard clay soil sample, described below, which had been spiked with a known concentration of a pesticide mixture. Solvent (hexane/acetone 1:1) was introduced into the cell and filled until 1 ml had passed through the cell into the collection vial. The extraction cell was pressurized with nitrogen at 2000 psi and placed in a block heater which had been set at 100° C. and held to equilibrate to the set temperature for 5 minutes. This was followed by a static hold time of 5 minutes at 2000 psi and 100° C. The valve was then opened to the collection vial; approximately 2 ml of flush fluid solvent was forced into the cell followed by a nitrogen purge of solvent and analytes into the collection vial. The final volume of solvent and analytes collected in the collection vial was from 13 to 15 ml. The collected fluid was concentrated to 1 ml by an inert gas blow-down. Aliquots of the concentrated sample were injected into a GC/MS for analysis. The results are shown in Table 3.

The spiked soil samples were prepared by Environmental Resource Associates (ERA, Arvada, CO). The range of soil types is representative of the soil samples analyzed for pesticides and semivolatiles by environmental laboratories. Spiking occurred at three levels: low level (5 µg/kg, the quantitation limit), mid level (250 µg/kg), and high level (2500 µg/kg). This simulates the range of contaminant levels found in typical soil samples. The three samples provided by ERA were designated: clay (ERA topsoil with approximately 60% clay, 40% sand); loam (90% ERA topsoil, 10% Ottawa sand); and said (80% ERA topsoil, 20% sand). Twenty compounds were spiked for the chlorinated pesticide analyses and fifty-seven compounds were spiked for the semi-volatile analyses. All samples were extracted without further preparation. Samples were extracted in parallel by automated Soxhlet extraction and by Accelerated Solvent Extraction (ASE, the method of the present invention). Once extracted, the samples were concentrated by a inert gas blow-down to 1 ml for the low level sample and 10 ml for the mid level sample, and the high level sample was diluted with solvent system to 25 mls prior to analysis.

TABLE 2

| Extraction Parameter | Pesticide Conditions | Fat Extraction Conditions |
| --- | --- | --- |
| Solvent | hexane/acetone (1:1) | chloroform |
| Temperature (°C.) | 100 | 75 |
| Pressure (psi) | 2000 | 2500 |
| Hold time | 5 min heat-up; 5 min static | Step 1) 10 min static, 6 min dynamic; 2) 10 min static, 6 min dynamic; 3) 10 min static, 12 min dynamic |
| Flush time | 15 sec | 30 sec |

TABLE 2-continued

| Extraction Parameter | Pesticide Conditions | Fat Extraction Conditions |
|---|---|---|
| Gas purge | 25 sec at 150 psi | 30 sec at 150 psi |
| Final Extraction volume (ml; equals extraction volume plus flush volume) | 13 to 15 | 15 |
| Sample size | 10 gm mid and high levels; 14 gm for high levels | 2 gm |
| Cell size | 10.4 ml | 3.5 ml |
| Post extraction volume adjustment (from ~15 mls) | 1 ml for low level; 10 ml for mid level; 25 ml for high level | no adjustment |

TABLE 3

ASE Recovery as % of Soxtec BNAs

| | | CLAY | | | LOAM | | | SAND | | |
|---|---|---|---|---|---|---|---|---|---|---|
| # | COMPOUND | LOW | MID | HIGH | LOW | MID | HIGH | LOW | MID | HIGH | AVE |
| 1 | Phenol | 93.3 | 78.7 | 135.9 | 13.9 | 82.8 | 124.6 | 108.8 | 130.6 | 89.7 | 102.0 |
| 2 | his(2-Chloroethyl)ether | 102.1 | 85.1 | 109.1 | 96.0 | 88.0 | 103.6 | 122.3 | 119.9 | 90.8 | 101.9 |
| 3 | 2-Chlorophenol | 100.8 | 82.6 | 115.0 | 93.8 | 88.9 | 111.1 | 115.0 | 115.3 | 91.9 | 101.6 |
| 4 | 1,3-Dichlorobenzene | 127.7 | 129.7 | 110.0 | — | 129.9 | 119.0 | — | — | 107.1 | 120.6 |
| 5 | 1,4-Dichlorobenzene | 127.9 | 127.0 | 110.5 | — | 127.8 | 116.4 | — | — | 105.8 | 119.2 |
| 6 | 1,2-Dichlorobenzene | 116.8 | 115.8 | 101.3 | — | 113.4 | 105.5 | — | 131.0 | 100.1 | 112.5 |
| 7 | 2-Methylphenol | 98.9 | 82.1 | 119.7 | 87.6 | 89.4 | 111.0 | 133.2 | 128.0 | 92.1 | 104.7 |
| 8 | bis(2-Chloroisopropyl)ether | 109.4 | 71.5 | 108.0 | 81.8 | 81.0 | 88.6 | 118.1 | 148.3 | 94.8 | 100.2 |
| 9 | a-Toludene | 100.0 | 89.7 | 117.2 | 100.0 | 152.5 | 120.3 | 100.0 | — | 102.7 | 110.3 |
| 10 | N-Nitroso-di-n-propylamine | 103.0 | 79.1 | 107.7 | 83.9 | 88.1 | 96.2 | 109.9 | 123.3 | 91.4 | 98.1 |
| 11 | Hexachloroethane | 97.1 | 125.1 | 111.0 | — | 117.1 | 128.1 | — | 147.9 | 103.7 | 118.6 |
| 12 | Nitrobenzene | 104.8 | 82.4 | 106.6 | 86.8 | 84.6 | 101.7 | 119.7 | 122.1 | 93.3 | 100.2 |
| 13 | Isophorone | 100.0 | 86.4 | 98.2 | 87.1 | 87.5 | 109.7 | 135.5 | 118.4 | 92.7 | 101.7 |
| 14 | 2,4-Dimethylphenol | 100.0 | 104.5 | 140.0 | 100.0 | 114.4 | 123.1 | 100.0 | — | 96.3 | 109.8 |
| 15 | 2-Nitrophenol | 80.7 | 80.5 | 107.9 | 91.4 | 88.7 | 103.2 | 122.1 | 107.1 | 87.0 | 96.3 |
| 16 | bis(Chlorethoxy)methane | 94.4 | 80.6 | 94.7 | 86.5 | 84.4 | 99.6 | 130.6 | 110.7 | 93.2 | 97.2 |
| 17 | 2,4-Dichlorophenol | 89.9 | 87.8 | 111.4 | 85.0 | 87.6 | 103.5 | 123.3 | 107.0 | 92.1 | 98.6 |
| 18 | 1,2,4-Trichlorobenzene | 98.0 | 97.8 | 98.8 | 123.0 | 93.7 | 94.5 | 137.0 | 99.4 | 95.3 | 104.2 |
| 19 | Naphthalene | 101.7 | 97.2 | 123.6 | 113.2 | 102.9 | 129.5 | — | 114.0 | 89.8 | 106.1 |
| 20 | 4-Chloroaniline | 100.0 | — | — | 100.0 | 125.5 | — | 100.0 | — | 114.9 | 108.1 |
| 21 | Hexachlorobutadiene | 101.1 | 98.7 | 102.2 | 124.1 | 90.3 | 98.0 | 131.9 | 96.1 | 96.8 | 104.7 |
| 22 | 4-Chloro-3-methylphenol | 90.4 | 80.2 | 114.7 | 79.0 | 85.2 | 109.8 | 131.6 | 116.2 | 90.1 | 99.7 |
| 23 | 2-Methylnaphthalene | 93.2 | 89.9 | 94.6 | 104.1 | 92.2 | 105.9 | 146.2 | 99.1 | 93.3 | 102.1 |
| 24 | Hexachlorocyclopentadiene | 100.0 | 100.0 | 0.0 | 100.0 | 100.0 | 6.8 | 100.0 | 100.0 | — | 75.8 |
| 25 | 2,4,6-Trichlorophenol | 94.6 | 90.0 | 112.0 | 84.2 | 91.2 | 103.6 | 101.5 | 95.9 | 89.8 | 95.9 |
| 26 | 2,4,5-Trichlorophenol | 84.4 | 91.9 | 109.6 | 96.1 | 80.7 | 103.6 | 108.9 | 83.9 | 87.9 | 94.1 |
| 27 | 2-Chloronaphthalene | 100.0 | 91.3 | 93.6 | 97.6 | 93.4 | 98.3 | 106.8 | 93.0 | 92.0 | 96.2 |
| 28 | 2-Nitroaniline | 90.0 | 83.4 | 97.4 | 71.3 | 88.4 | 89.9 | 112.1 | 113.3 | 87.7 | 92.6 |
| 29 | 2,6-Dinitrotoluene | 83.1 | 90.6 | 91.6 | 86.4 | 90.6 | 90.3 | 104.3 | 84.7 | 90.9 | 90.3 |
| 30 | Acenaphthylene | 104.9 | 95.9 | 100.5 | 99.0 | 97.9 | 108.8 | 118.5 | 97.8 | 92.0 | 101.7 |
| 31 | 3-Nitroaniline | — | 115.6 | 97.6 | 100.0 | 111.8 | 107.8 | 0.0 | 111.7 | 99.0 | 92.9 |
| 32 | Acenaphthene | 102.1 | 92.6 | 97.6 | 97.2 | 96.9 | 104.4 | 114.2 | 92.0 | 89.0 | 98.4 |
| 33 | 4-Nitrophenol | 0.0 | 93.2 | 121.5 | 18.1 | 87.1 | 116.6 | 69.1 | 90.5 | 84.5 | 75.0 |
| 34 | 2,4-Dinitrotoluene | 73.9 | 91.9 | 100.2 | 84.7 | 93.8 | 98.9 | 100.9 | 84.3 | 87.3 | 90.7 |
| 35 | Dibenzofuran | 89.5 | 91.7 | 109.3 | 98.5 | 92.2 | 111.4 | 113.8 | 92.7 | 90.4 | 98.8 |
| 36 | 4-Chlorophenyl-phenylether | 83.0 | 94.5 | 98.7 | 95.7 | 94.3 | 94.2 | 111.4 | 87.7 | 90.3 | 94.4 |
| 37 | Fluorene | 85.2 | 94.0 | 80.2 | 102.0 | 95.5 | 103.8 | 121.3 | 85.7 | 90.9 | 95.4 |
| 38 | 4-Nitroaniline | 77.8 | 114.8 | 94.5 | 129.6 | 103.6 | 95.1 | — | 89.3 | 87.6 | 99.1 |
| 39 | N-Nitrosodiphenylamine | 82.6 | 96.7 | 93.8 | 92.9 | 93.4 | 116.4 | 97.5 | 110.9 | 86.7 | 96.8 |
| 40 | 4-Bromophenyl-phenylether | 86.6 | 92.9 | 92.8 | 91.1 | 107.6 | 89.4 | 118.0 | 97.5 | 87.1 | 95.8 |
| 41 | Hexachlorobenzene | 95.4 | 91.7 | 92.3 | 95.4 | 93.6 | 83.7 | 106.8 | 94.3 | 90.0 | 93.7 |
| 42 | Pentachlorophenol | 68.2 | 85.9 | 107.7 | 53.2 | 89.8 | 88.1 | 95.6 | 59.8 | 81.3 | 81.2 |
| 43 | Phenanthrene | 92.1 | 93.7 | 93.3 | 100.0 | 97.8 | 113.3 | 124.4 | 101.0 | 89.9 | 100.6 |
| 44 | Anthracene | 101.6 | 95.0 | 93.5 | 92.5 | 101.8 | 118.4 | 123.0 | 94.5 | 90.6 | 101.2 |
| 45 | Carbazole | 04.4 | 00.3 | 06.6 | 105.5 | 06.7 | 111.4 | 115.7 | 83.2 | 88.9 | 00.1 |
| 46 | Fluoranthene | 109.9 | 101.4 | 94.3 | 111.8 | 96.6 | 109.6 | 123.2 | 85.1 | 92.7 | 102.7 |
| 47 | Pyrene | 106.5 | 105.8 | 107.6 | 116.7 | 90.7 | 127.5 | 103.4 | 95.5 | 93.2 | 105.2 |
| 48 | 3,3'-Dichlorobenzidine | 100.0 | — | 131.4 | 100.0 | — | 107.6 | 100.0 | — | 100.0 | 116.5 |
| 49 | Benzo(e)enthracene | 98.1 | 107.0 | 98.4 | 119.3 | 98.6 | 104.0 | 105.0 | 93.4 | 89.3 | 101.5 |
| 50 | Chrysene | 100.0 | 108.5 | 100.2 | 116.8 | 93.0 | 117.0 | 106.7 | 93.6 | 90.2 | 102.9 |
| 51 | Benzo(b)fluoranthene | 106.6 | 109.9 | 75.6 | 121.7 | 100.7 | 93.9 | 106.9 | 81.9 | 93.8 | 99.0 |

TABLE 3-continued

| | | ASE Recovery as % of Soxtec BNAs | | | | | | | | |
|---|---|---|---|---|---|---|---|---|---|---|
| | | CLAY | | | LOAM | | | SAND | | |
| # | COMPOUND | LOW | MID | HIGH | LOW | MID | HIGH | LOW | MID | HIGH | AVE |
| 52 | Benzo(k)fluoranthene | 102.4 | 106.2 | 88.4 | 125.5 | 99.4 | 95.1 | 144.7 | 89.2 | 78.1 | 103.1 |
| 53 | Benzo(s)pyrene | 107.9 | 105.5 | 80.8 | 122.3 | 97.7 | 104.6 | 101.7 | 86.2 | 92.0 | 99.9 |
| 54 | Indeno(1,2,3-cd)pyrene | 95.1 | 105.7 | 93.8 | 126.0 | 105.2 | 90.4 | 133.6 | 82.6 | 91.9 | 102.7 |
| 55 | Dibenz(a,h)anthracene | 85.0 | 102.6 | 82.0 | 116.8 | 100.7 | 91.9 | 142.3 | 71.0 | 93.1 | 98.6 |
| 56 | Benzo(g,h,i)perylen | 98.0 | 0.0 | 81.2 | 0.0 | 33.6 | 78.6 | 128.7 | 83.0 | 94.2 | 66.4 |
| | Average | 95.1 | 94.3 | 101.0 | 95.5 | 96.5 | 104.1 | 113.0 | 100.9 | 92.5 | |

The dashes (—) indicate values above 150%. These values were not used to determine the average. The 0% values were used.

Example 2

Extraction of Fat from Foods

The extraction system was set up as in Example 1 with the conditions set as shown in Table 2. The sample was a commercial popcorn snack containing cheese. Samples were extracted by ASE and data compared to extraction using Soxhlet.

The amount of fat was determined in two ways: 1) the total fat collected in the vials was weighed after extraction, and 2) the amount of fat extracted was determined by the difference in weight of the extraction cell before and after extraction. The recovery of fat compared to Soxhlet determination on an aliquot of the same sample was 91.1% by weight of the fat collected and 97.8% by weight determined by the extraction cell difference method.

TABLE 4

Table 4 presents a summary of the different analytes, samples and solvent systems tested.

| Analyte | Sample | Solvent System | Temp °C. | Pressure psi | Time of Extraction |
|---|---|---|---|---|---|
| Total petroleum hydrocarbons (TPH) | soil, shale | perchloroethylene | 60–100 | 500–2500 | |
| Polychlorinated biphenyls (PCB) | soil, sediment, sludge, animal tissue | isooctane; hexane/acetone (1:1) | 75–100 | 1200–2500 | |
| Gasoline (BTEX) | soil | methylene chloride | 50–75 | 1200–2500 | |
| Chlorinated pesticides | soil | hexane/acetone (1:1) | 50–100 | 1200–2500 | |
| Triazine herbicides | soil | hexane/acetone (1:1); methanol; methylene chloride/ acetone (1:1) | 50–150 | 1200–2500 | |
| Triglycerides (lipids) | foods, grains | chloroform; hexane; hexane/acetone (1:1) | 50–150 | 500–2500 | |
| Polymer additives | polymers | methylene chloride; ethanol/toluene/ acetone (1:1:1) | 50–150 | 500–2500 | |
| Phenols | soil | hexane/acetone (1:1); methanol | 50–100 | 500–2500 | |
| "Semi-volatiles"* | soils | hexane/acetone (1:1) | 50–100 | 500–2500 | |

*As defined by EPA method 8270, this includes compounds in the following classes: PAHs, phenols, chlorinated hydrocarbons, nitrosamines, anilines, phthalates, halogenated ethers, carbazoles, phenylamines, nitrates hydrocarbons and benzidines.

We claim:

1. An analytical method for solvent extraction of organic analytes from a sample and for analyzing organic analytes, said method comprising, (a) maintaining a sample containing organic analytes in contact with an extraction fluid consisting essentially of a non-aqueous organic solvent system in an extraction cell under elevated temperatures and pressures below supercritical conditions for a sufficient time to substantially non-selectively extract said organic analytes from said sample, said organic solvent system being in liquid form under standard conditions of temperature and pressure and during extraction, said extraction pressure being at least about 100 psi, the volumetric ratio of said organic solvent system to said extraction cell being no greater than 5:1, and (b) removing said extracted organic analytes dissolved in said organic solvent system without further extraction, by flowing a purge fluid through the extraction cell, said extraction cell being maintained at a constant volume during steps (a) and (b), and (c) analyzing said removed, extracted organic analytes.

2. The method of claim 1 in which said organic solvent system comprises one organic solvent.

3. The method of claim 1 in which said organic solvent system comprises at least two organic solvents.

4. The method of claim 1 in which said organic solvent system has an average viscosity of about 0.20 to about 4.20 cps at 25° C.

5. The method of claim 1 in which said organic solvent system is characterized by a ratio of its average viscosity at room temperature to its average viscosity at the temperature of step (a) of at least about 2 to about 15.

6. The method of claim 2 in which the maximum pressure is about 2500 psi.

7. The method of claim 1 in which said sample substantially fills said extraction cell.

8. The method of claim 1 wherein said extraction cell is substantially full of a mixture comprising the sample and an inert filler.

9. The method of claim 1 in which the temperature in °K in step (a) is maintained at a level of about 0.8 to 2.0 times the average boiling point in °K of the organic solvent system under standard conditions of pressure.

10. The method of claim 1 in which, after 15 minutes of maintaining the conditions of step (a), no greater than about 10% more of said analytes would be extracted in said organic solvent system by maintaining the same conditions for one additional hour.

11. The method of claim 1 in which the polarity index of said solvent system ranges between the polarities of pentane (polarity index of 0.0) and of dimethylsulfoxide (polarity index of 7.2).

12. The method of claim 1 in which the dielectric constant of said solvent system ranges between the dielectric constant of hexane (1.88) and of propylene carbonate (69.0).

13. The method of claim 1 in which the dipole moment of said solvent system ranges between the dipole moment of trimethylpentane (iso-octane) at 0.0 Debye and of N-methylpyrrolidone at 4.09 Debye.

14. The method of claim 1 in which the eluotropic value on alumina of said solvent system ranges between the eluotropic value of pentane (0.0) and of methanol (0.95).

15. The method of claim 1 in which said organic solvent system contains one or more organic solvents, each having a boiling point less than 100° C. at standard conditions of pressure.

16. The method of claim 1 in which said organic solvent system comprises one or more organic solvents selected from the group consisting of perchloroethylene, isooctane, hexane, acetone, methylene chloride, toluene, methanol, chloroform, ethanol, tetrahydrofuran, acetonitrile, methyl ethyl ketone, pentane, N-methylpyrrolidone, cyclohexane, dimethyl formamide, xylene, ethyl acetate, chlorobenzene, methoxyethanol, morpholine, pyridine, piperidine, dimethylsulfoxide, ethoxyethanol, isopropanol, propylene carbonate, petroleum ether, diethyl ether, dioxane, and mixtures thereof.

17. The method of claim 16 wherein said organic solvent system contains an additive.

18. The method of claim 17 wherein said additive is selected from the group consisting of trifluoroacetic acid, citric acid, acetic acid, trimethyl amine, and trimethyl ammonium hydroxide.

19. The method of claim 1 in which said purge fluid comprises an inert gas, said method further comprising (c) collecting said solvent containing said analytes in a container under an atmosphere of said inert gas.

20. The method of claim 1 in which said organic solvent system has a Hildebrand solubility parameter between the solubility parameter of pentane (7.05) and of methanol (14.0).

21. The method of claim 1 in which said analytes include at least one analyte selected from the group consisting of a pesticide, an herbicide, a PCB, a PAH, and gasoline.

22. The method of claim 1 in which the temperature within the extraction cell is maintained at about 50° C. to 150° C. during extraction.

23. The method of claim 1 in which not more than 10% of the total of said analytes will be subsequently extracted by repeated extraction of the same sample using the method of claim 1 or other extraction methods.

24. The method of claim 1 in which said analytes are detected.

25. The method of claim 1 in which step (a) is performed in the absence of microwave energy.

26. The method of claim 1 wherein said sufficient time ranges from about 10 minutes to about 30 minutes.

27. The method according to claim 1 wherein said flow rate ranges from about 0.1 mls/min to about 0.5 mls/min.

28. The method according to claim 1 wherein after step (a) a flush fluid is flowed through said cell prior to the purge fluid.

29. The method according to claim 28 in which said flush liquid comprises a non-aqueous organic solvent system.

30. The method of claim 1 which said purge fluid comprises a gas.

31. The method of claim 30 in which said gas is an inert gas.

32. The method of claim 1 in which said organic solvent system comprises at least one organic solvent in which said organic analytes are known to be soluble.

33. The method of claim 1 in which the analysis of step (c) is performed by a technique selected from the group consisting of gas chromatography, mass spectrometry, ion chromatography, liquid chromatography and capillary electrophoresis.

34. The method of claim 1 in which the pressure during step (b) is substantially lower than the pressure during step (a).

35. The method according to claim 1 in which said pressure is no greater than about 2500 psi.

* * * * *

UNITED STATES PATENT AND TRADEMARK OFFICE
CERTIFICATE OF CORRECTION

PATENT NO.   :   5,843,311
DATED        :   December 1, 1998
INVENTOR(S)  :   RICHTER et al.

It is certified that error appears in the above-indentified patent and that said Letters Patent is hereby corrected as shown below:

On the title page,

[75] Inventors: please delete "Nebojsha" and insert --Nebojsa--.

Signed and Sealed this

Eleventh Day of April, 2000

Attest:

Attesting Officer

Q. TODD DICKINSON

Director of Patents and Trademarks